(12) United States Patent
Jeppesen et al.

(10) Patent No.: US 6,369,055 B1
(45) Date of Patent: Apr. 9, 2002

(54) COMPOUNDS, THEIR PREPARATION AND USE

(75) Inventors: Lone Jeppesen, Virum; Per Sauerberg, Farum; Anthony Murray, Hellerup; Paul Stanley Bury, Copenhagen, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/551,701

(22) Filed: Apr. 18, 2000

Related U.S. Application Data
(60) Provisional application No. 60/133,089, filed on May 7, 1999.

(30) Foreign Application Priority Data

Apr. 20, 1999 (DK) .......................... 1999 00534

(51) Int. Cl.$^7$ .................... C07D 265/38; A61K 31/536
(52) U.S. Cl. ..................... 514/229.8; 544/102
(58) Field of Search ........................ 544/102; 514/229.8

(56) References Cited

FOREIGN PATENT DOCUMENTS

| EP | 0 903 343 A1 | 3/1999 |
|---|---|---|
| WO | WO 96/04260 | 2/1996 |
| WO | WO 96/04261 A1 | 2/1996 |
| WO | WO 97/25042 | 7/1997 |
| WO | WO 97/31907 | 9/1997 |
| WO | WO 99 08501 | 2/1999 |
| WO | WO 99/16758 | 4/1999 |
| WO | WO 99/19313 | 4/1999 |
| WO | WO 99/20614 | 4/1999 |
| WO | WO 99/38850 | 8/1999 |

OTHER PUBLICATIONS

Abstract of Japanese Patent JP 10182550 (1998).

*Primary Examiner*—Bruck Kifle
(74) *Attorney, Agent, or Firm*—Reza Green, Esq.; Peter J. Waibel, Esq.

(57) ABSTRACT

The present invention relates to compounds of the general formula (I)

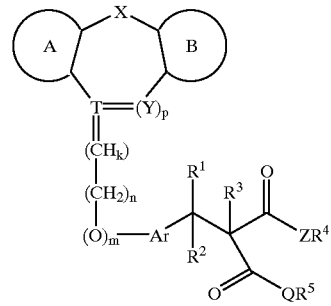

The compounds are useful in the treatment and/or prevention of conditions mediated by nuclear receptors, in particular the Peroxisome Proliferator-Activated Receptors (PPAR).

16 Claims, No Drawings

COMPOUNDS, THEIR PREPARATION AND USE

CROSS-REFERENCE TO RELATED APPLICATIONS

This application claims priority under 35 U.S.C. 119 of Danish application PA 1999 00534 filed on Apr. 20, 1999, and U.S. application Ser. No. 60/133,089 filed on May 7, 1999, the contents of which are fully incorporated herein by reference.

FIELD OF INVENTION

The present invention relates to novel compounds, pharmaceutical compositions containing them, methods for preparing the compounds and their use as medicaments. More specifically, compounds of the invention can be utilised in the treatment and/or prevention of conditions mediated by nuclear receptors, in particular the Peroxisome Proliferator-Activated Receptors (PPAR).

BACKGROUND OF THE INVENTION

Coronary artery disease (CAD) is the major cause of death in Type 2 diabetic and metabolic syndrome patients (i.e. patients that fall within the 'deadly quartet' category of impaired glucose tolerance, insulin resistance, hypertriglyceridaemia and/or obesity).

The hypolipidaemic fibrates and antidiabetic thiazolidinediones separately display moderately effective triglyceride-lowering activities although they are neither potent nor efficacious enough to be a single therapy of choice for the dyslipidaemia often observed in Type 2 diabetic or metabolic syndrome patients. The thiazolidinediones also potently lower circulating glucose levels of Type 2 diabetic animal models and humans. However, the fibrate class of compounds are without beneficial effects on glycaemia. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key-players in regulation of plasma triglyceride content. Fibrates, on the one hand, are PPARα activators, acting primarily in the liver. Thiazolidinediones, on the other hand, are high affinity ligands for PPARγ acting primarily on adipose tissue.

Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPARγ activation in initiating and regulating this cell differentiation. Several highly specialised proteins are induced during adipocyte differentiation, most of them being involved in lipid storage and metabolism. The exact link from activation of PPARγ to changes in glucose metabolism, most notably a decrease in insulin resistance in muscle, has not yet been clarified. A possible link is via free fatty acids such that activation of PPARγ induces Lipoprotein Lipase (LPL), Fatty Acid Transport Protein (FATP) and Acyl-CoA Synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence.

PPARα is involved in stimulating β-oxidation of fatty acids. In rodents, a PPARα-mediated change in the expression of genes involved in fatty acid metabolism lies at the basis of the phenomenon of peroxisome proliferation, a pleiotropic cellular response, mainly limited to liver and kidney and which can lead to hepatocarcinogenesis in rodents. The phenomenon of peroxisome proliferation is not seen in man. In addition to its role in peroxisome proliferation in rodents, PPARα is also involved in the control of HDL cholesterol levels in rodents and humans. This effect is, at least partially, based on a PPARα-mediated transcriptional regulation of the major HDL apolipoproteins, apo A-I and apo A-II. The hypotriglyceridemic action of fibrates and fatty acids also involves PPARα and can be summarised as follows: (I) an increased lipolysis and clearance of remnant particles, due to changes in lipoprotein lipase and apo C-III levels, (II) a stimulation of cellular fatty acid uptake and their subsequent conversion to acyl-CoA derivatives by the induction of fatty acid binding protein and acyl-CoA synthase, (III) an induction of fatty acid-oxidation pathways, (IV) a reduction in fatty acid and triglyceride synthesis, and finally (V) a decrease in VLDL production. Hence, both enhanced catabolism of triglyceride-rich particles as well as reduced secretion of VLDL particles constitutes mechanisms that contribute to the hypolipidemic effect of fibrates.

A number of compounds have been reported to be useful in the treatment of hyperglycemia, hyperlipidemia and hypercholesterolemia (U.S. Pat. No. 5,306,726, PCT Publications Nos. WO 91/19702, WO 95/03038, WO 96/04260, WO 94/13650, WO 94/01420, WO 97/36579, WO 97/25042, WO 95/17394, WO 99/08501, WO 99/19313 and WO 99/16758).

SUMMARY OF THE INVENTION

Glucose lowering as a single approach does not overcome the macrovascular complications associated with Type 2 diabetes and metabolic syndrome. Novel treatments of Type 2 diabetes and metabolic syndrome must therefore aim at lowering both the overt hypertriglyceridarmia associated with these syndromes as well as alleviation of hyperglycaemia.

The clinical activity of fibrates and thiazolidinediones indicates that research for compounds displaying combined PPARα and PPARγ activation should lead to the discovery of efficacious glucose and triglyceride lowering drugs that have great potential in the treatment of Type 2 diabetes and the metabolic syndrome (i.e. impaired glucose tolerance, insulin resistance, hypertriglyceridaemia and/or obesity).

DETAILED DESCRIPTION OF THE INVENTION

Accordingly, the present invention relates to compounds of the general formula (I):

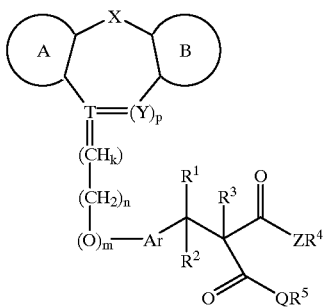

wherein ring A and ring B, fused to the ring containing X and T, independently of each other represents a 5–6 membered cyclic ring, optionally substituted with one or more halogen, perhalomethyl, hydroxy, nitro, cyano, formyl, or $C_{1-12}$-alkyl, $C_{4-12}$-alkenynyl, $C_{2-12}$-alkenyl, $C_{2-12}$-alkynyl, $C_{1-12}$-alkoxy, aryloxy, arylalkyl, arylalkoxy, heteroarylalkyl, heteroaryloxy, heteroarylalkoxy, acyl, acyloxy, hydroxy$C_{1-12}$-alkyl, amino, acylamino, $C_{1-2}$-alkyl-amino, arylamino, arylalkylamino, amino-$C_{1-12}$-alkyl, $C_{1-12}$-alkoxycarbonyl, aryloxycarbonyl, arylalkoxycarbonyl, $C_{1-12}$-alkoxy$C_{1-12}$-alkyl, aryloxy$C_{1-12}$-alkyl, arylalkoxy$C_{1-12}$-alkyl, $C_{1-12}$-alkylthio, thio$C_{1-12}$-alkyl, $C_{1-12}$-alkoxycarbonylamino, aryloxycarbonylamino, arylalkoxycarbonylamino, bicycloalkyl, $(C_{3-6}$-cycloalkyl$)C_{1-6}$-alkyl, $C_{1-6}$-dialkylamino, $C_{1-6}$-alkylsulfonyl, $C_{1-6}$-monoalkylaminosulfonyl, $C_{1-6}$-dialkylaminosulfonyl, arylthio, arylsulfonyl, $C_{1-6}$-monoalkylaminocarbonyl, $C_{1-6}$-dialkylaminocarbonyl, $-COR^6$ or $-SO_2R^7$, wherein $R^6$ and $R^7$ independently of each other are selected from hydroxy, halogen, perhalomethyl, $C_{1-6}$-alkoxy or amino optionally substituted with one or more $C_{1-6}$-alkyl or perhalomethyl; or aryl, wherein the aryl optionally can be substituted with one or more halogen, perhalomethyl, hydroxy, nitro or cyano; or heteroaryl, wherein the heteroaryl optionally can be substituted with halogen, amino hydroxy, $C_{1-6}$-alkyl or $C_{1-6}$-alkoxy; or heterocyclyl, wherein the heterocyclyl optionally can be substituted with halogen, amino, hydroxy, $C_{1-6}$-alkyl or $C_{1-6}$-alkoxy;

X is $-O-$, $-S-$ or $-(NR^8)-$ wherein $R^8$ is hydrogen, halogen, hydroxy, nitro, cyano, formyl, $C_{1-12}$-alkyl, $C_{1-12}$-alkoxy, aryl, aryloxy, arylalkyl, arylalkoxy, heterocyclyl, heteroaryl, heteroarylalkyl, heteroaryloxy, heteroarylalkoxy, acyl, acyloxy, hydroxyalkyl, amino, acylamino, $C_{1-12}$-alkyl-amino, arylamino, arylalkylamino, amino$C_{1-12}$-alkyl, $C_{1-12}$-alkoxycarbonyl, aryloxycarbonyl, arylalkoxycarbonyl, $C_{1-12}$-alkoxy$C_{1-12}$-alkyl, aryloxy$C_{1-12}$-alkyl, arylalkoxy$C_{1-12}$-alkyl, $C_{1-12}$-alkylthio, thio$C_{1-12}$-alkyl, $C_{1-12}$-alkoxycarbonylamino, aryloxycarbonylamino, arylalkoxycarbonylamino, $-COR^9$ or $-SO_2R^{10}$, wherein $R^9$ and $R^{10}$ independently of each other are selected from hydroxy, halogen, $C_{1-6}$-alkoxy, amino optionally substituted with one or more $C_{1-6}$-alkyl, perhalomethyl or aryl;

T is N or $CR^{14}$, wherein $R^{14}$ is hydrogen, $C_{1-12}$-alkoxy, $C_{1-12}$-alkyl, $C_{4-12}$-alkenynyl, $C_{2-12}$-alkenyl, $C_{2-12}$-alkynyl, aryl or arylalkyl;

Y is C, O, S, CO, SO, $SO_2$ or $NR^{11}$, wherein $R^{11}$ is hydrogen, $C_{1-6}$-alkyl;

k is 1 or 2;

Ar represents arylene, heteroarylene, or a divalent heterocyclic group each of which can optionally be substituted with one or more halogen, $C_{1-6}$-alkyl, amino, hydroxy, $C_{1-6}$-alkoxy or aryl;

$R^1$ represents hydrogen, hydroxy, halogen, $C_{1-12}$-alkoxy, $C_{1-12}$-alkyl, $C_{4-12}$-alkenynyl, $C_{2-12}$-alkenyl, $C_{2-12}$-alkynyl or arylalkyl; optionally substituted with one or more halogen, perhalomethyl, hydroxy, nitro or cyano;

$R^2$ represents hydrogen, hydroxy, halogen, $C_{1-12}$-alkoxy, $C_{1-12}$-alkyl, $C_{4-12}$-alkenynyl, $C_{2-12}$-alkenyl, $C_{2-12}$-alkynyl or arylalkyl; optionally substituted with one or more halogen, perhalomethyl, hydroxy, nitro or cyano; or $R^2$ forms a bond together with $R^3$;

$R^3$ represents hydrogen, hydroxy, halogen, $C_{1-12}$-alkoxy, $C_{1-12}$-alkyl, $C_{4-12}$-alkenynyl, $C_{2-12}$-alkenyl, $C_{2-12}$-alkynyl, acyl or arylalkyl; optionally substituted with one or more halogen, perhalomethyl, hydroxy, nitro or cyano; or $R^3$ forms a bond together with $R^2$;

$R^4$ represents hydrogen, $C_{1-12}$-alkyl, $C_{4-12}$-alkenynyl, $C_{2-12}$-alkenyl, $C_{2-12}$-alkynyl, aryl, arylalkyl, heterocyclyl, heteroaryl or heteroarylalkyl groups; optionally substituted with one or more halogen, perhalomethyl, hydroxy, nitro or cyano;

$R^5$ represents hydrogen, $C_{1-12}$-alkyl, $C_{4-12}$-alkenynyl, $C_{2-12}$-alkenyl, $C_{2-12}$-alkynyl, aryl, arylalkyl, heterocyclyl, heteroaryl or heteroarylalkyl groups; optionally substituted with one or more halogen, perhalomethyl, hydroxy, nitro or cyano;

Z represents oxygen or $NR^{12}$, wherein $R^{12}$ represents hydrogen $C_{1-12}$-alkyl, aryl, hydroxy$C_{1-12}$-alkyl or arylalkyl groups or when Z is $NR^{12}$, $R^4$ and $R^{12}$ may form a 5 or 6 membered nitrogen containing ring, optionally substituted with one or more $C_{1-6}$-alkyl;

Q represents oxygen or $NR^{13}$, wherein $R^{13}$ represents hydrogen $C_{1-12}$-alkyl, aryl, hydroxy$C_{1-12}$-alkyl or arylalkyl groups or when Q is $NR^{13}$, $R^5$ and $R^{13}$ may form a 5 or 6 membered nitrogen containing ring, optionally substituted with one or more $C_{1-6}$-alkyl;

n is an integer ranging from 0 to 3;

m is an integer ranging from 0 to 1;

p is an integer ranging from 0 to 1;

or a salt thereof with a pharmaceutically acceptable acid or base, or any optical isomer or mixture of optical isomers, including a racemic mixture, or any tautomeric forms.

In a preferred embodiment, the present invention is concerned with compounds of formula I wherein ring A and ring B, fused to the ring containing X and T independently of each other represents a 5–6 membered cyclic ring, optionally substituted with halogen, $C_{1-6}$-alkyl or aryl, wherein the aryl can be substituted with one or more halogen or $C_{1-6}$-alkyl; or heterocyclyl, wherein the heterocyclyl can be substituted with $C_{1-6}$-alkyl.

In another preferred embodiment, the present invention is concerned with compounds of formula I wherein ring A and ring B, fused to the ring containing X and T independently of each other represents a 5–6 membered cyclic ring.

In another preferred embodiment, the present invention is concerned with compounds of formula I wherein ring A and ring B, fused to the ring containing X and T independently of each other represents aryl.

In another preferred embodiment, the present invention is concerned with compounds of formula I wherein X is O.

In another preferred embodiment, the present invention is concerned with compounds of formula I wherein T is N.

In another preferred embodiment, the present invention is concerned with compounds of formula I wherein k is 2.

In another preferred embodiment, the present invention is concerned with compounds of formula I wherein = represents a single bond.

In another preferred embodiment, the present invention is concerned with compounds of formula I wherein Ar represents arylene.

In another preferred embodiment, the present invention is concerned with compounds of formula I wherein $R^1$, $R^2$ and $R^3$ represents hydrogen.

In another preferred embodiment, the present invention is concerned with compounds of formula I wherein $R^4$ and $R^5$ represents hydrogen or methyl.

In another preferred embodiment, the present invention is concerned with compounds of formula I wherein Z and Q represents O.

In another preferred embodiment, the present invention is concerned with compounds of formula I wherein n is 1.

In another preferred embodiment, the present invention is concerned with compounds of formula I wherein m is 1.

In another preferred embodiment, the present invention is concerned with compounds of formula I wherein p is 0.

Preferred compounds of the invention are:

2-{4-(2-Phenoxazine-10-yl-ethoxy)-benzyl]-malonic acid dimethyl ester,
2-{4-(2-Phenoxazine-10-yl-ethoxy)-benzyl]-malonic acid;

or a salt thereof with a pharmaceutically acceptable acid or base, or any optical isomer or mixture of optical isomers, including a racemic mixture, or any tautomeric forms.

In the above structural formulas and throughout the present specification, the following terms have the indicated meaning:

The terms "$C_{1-12}$-alkyl" as used herein, alone or in combination is intended to include those alkyl groups of the designated length in either a linear or branched or cyclic configuration represents e.g. cyclopropyl, cyclobutyl, cyclopentyl, cyclohexyl, cycloheptyl and cyclooctyl and the like. Typical $C_{1-6}$-alkyl groups include, but are not limited to, methyl, ethyl, n-propyl, iso-propyl, butyl, iso-butyl, sec-butyl, tert-butyl, pentyl, iso-pentyl, hexyl, iso-hexyl, cyclopropyl, cyclobutyl, cyclopentyl, cyclohexyl, cycloheptyl and cyclooctyl and the like.

The terms "$C_{2-n'}$-alkenyl" wherein n' can be from 3 through 15, as used herein, represents an olefinically unsaturated branched or straight group having from 2 to the specified number of carbon atoms and at least one double bond. Examples of such groups include, but are not limited to, vinyl, 1-propenyl, 2-propenyl, allyl, iso-proppenyl, 1,3-butadienyl, 1-butenyl, hexenyl, pentenyl and the like.

The terms "$C_{2-n'}$-alkynyl" wherein n' can be from 3 through 15, as used herein, represent an unsaturated branched or straight group having from 2 to the specified number of carbon atoms and at least one triple bond. Examples of such groups include, but are not limited to, 1-propynyl, 2-propynyl, 1-butynyl, 2-butynyl, 1-pentynyl, 2-pentynyl and the like.

The terms "$C_{4-n'}$-alkenynyl" wherein n' can be from 5 through 15, as used herein, represent an unsaturated branched or straight hydrocarbon group having from 4 to the specified number of carbon atoms and both at least one double bond and at least one triple bond. Examples of such groups include, but are not limited to, 1-penten-4-yne, 3-penten-1-yne, 1,3-hexadiene-5-yne and the like.

The term "$C_{1-12}$-alkoxy" as used herein, alone or in combination is intended to include those $C_{1-12}$-alkyl groups of the designated length in either a linear or branched or cyclic configuration linked thorough an ether oxygen having its free valence bond from the ether oxygen. Examples of linear alkoxy groups are methoxy, ethoxy, propoxy, butoxy, pentoxy, hexoxy and the like. Examples of branched alkoxy are isoprpoxy, sec-butoxy, tert-butoxy, isopentoxy, isohexoxy and the like. Examples of cyclic alkoxy are cyclopropyloxy, cyclobutyloxy, cyclopentyloxy, cyclohexyloxy and the like.

The term "$C_{1-12}$-alkylthio" as used herein, alone or in combination, refers to a straight or branched or cyclic monovalent substituent comprising a $C_{1-12}$-alkyl group linked through a divalent sulfur atom having its free valence bond from the sulfur atom and having 1 to 12 carbon atoms e.g. methylthio, ethylthio, propylthio, butylthio, pentylthio and the like. Examples of cyclic alkylthio are cyclopropylthio, cyclobutylthio, cyclopentylthio, cyclohexylthio and the like.

The term "$C_{1-12}$-alkylamino" as used herein, alone or in combination, refers to a straight or branched or cyclic monovalent substituent comprising a $C_{1-12}$-alkyl group linked through amino having a free valence bond from the nitrogen atom e.g. methylamino, ethylamino, propylamino, butylamino, pentylamino and the like. Examples of cyclic alkylamino are cyclopropylamino, cyclobutylamino, cyclopentylamino, cyclohexylamino and the like.

The term "hydroxy$C_{1-12}$-alkyl" as used herein, alone or in combination, refers to a $C_{1-12}$-alkyl as defined herein whereto is attached a hydroxy group, e.g. hydroxyethyl, 1-hydroxypropyl, 2-hydroxypropyl and the like.

The term "arylamino" as used herein, alone or in combination, refers to an aryl as defined herein linked through amino having a free valence bond from the nitrogen atom e.g. phenylamino, naphthylamino and the like.

The term "arylalkylamino" as used herein, alone or in combination, refers to an arylalkyl as defined herein linked through amino having a free valence bond from the nitrogen atom e.g. benzylamino, phenethylamino, 3-phenylpropylamino, 1-naphtylmethylamino, 2-(1-naphtyl)ethylamino and the like.

The term "amino$C_{1-12}$-alkyl" as used herein, alone or in combination, refers to a $C_{1-12}$-alkyl as defined herein whereto is attached an amino group, e.g. aminoethyl, 1-aminopropyl, 2-aminopropyl and the like.

The term "aryloxycarbonyl" as used herein, alone or in combination, refers to an aryloxy as defined herein linked through a carbonyl having a free valence bond from the carbon atom, e.g. phenoxycarbonyl, 1-naphthyloxycarbonyl or 2-naphthyloxycarbonyl and the like.

The term "arylalkoxycarbonyl" as used herein, alone or in combination, refers to an arylalkoxy as defined herein linked through a carbonyl having a free valence bond from the carbon atom, e.g. benzyloxycarbonyl, phenethoxycarbonyl, 3-phenylpropoxycarbonyl, 1-naphthylmethoxycarbonyl, 2-(1-naphtyl)ethoxycarbonyl and the like.

The term "$C_{1-12}$-alkoxy$C_{1-12}$-alkyl" as used herein, alone or in combination, refers to a $C_{1-12}$-alkyl as defined herein whereto is attached a $C_{1-12}$-alkoxy as defined herein, e.g. methoxymethyl, ethoxymethyl, methoxyethyl, ethoxyethyl and the like.

The term "aryloxy$C_{1-12}$-alkyl" as used herein, alone or in combination, refers to a $C_{1-12}$-alkyl as defined herein whereto is attached an aryloxy as defined herein, e.g. phenoxymethyl, phenoxydodecyl, 1-naphthyloxyethyl, 2-naphthyloxypropyl and the like.

The term "arylalkoxy$C_{1-12}$-alkyl" as used herein, alone or in combination, refers to a $C_{1-12}$-alkyl as defined herein whereto is attached an arylalkoxy as defined herein, e.g.

benzyloxymethyl, phenethoxydodecyl, 3-phenylpropoxyethyl, 1-naphthylmethoxypropyl, 2-(1-naphtyl)ethoxymethyl and the like.

The term "thio$C_{1-12}$-alkyl" as used herein, alone or in combination, refers to a $C_{1-12}$-alkyl as defined herein whereto is attached a group of formula —SR''' wherein R''' is hydrogen, $C_{1-6}$-alkyl or aryl, e.g. thiomethyl, methylthiomethyl, phenylthioethyl and the like.

The term "$C_{1-12}$-alkoxycarbonylamino" as used herein, alone or in combination, refers to a $C_{1-12}$-alkoxycarbonyl as defined herein linked through amino having a free valence bond from the nitrogen atom e.g. methoxycarbonylamino, carbethoxyamino, propoxycarbonylamino, isopropoxycarbonylamino, n-butoxycarbonylamino, tert-butoxycarbonylamino and the like.

The term "aryloxycarbonylamino" as used herein, alone or in combination, refers to an aryloxycarbonyl as defined herein linked through amino having a free valence bond from the nitrogen atom e.g. phenoxycarbonylamino, 1-naphthyloxycarbonylamino or 2-naphthyloxycarbonylamino and the like.

The term "arylalkoxycarbonylamino" as used herein, alone or in combination, refers to an arylalkoxycarbonyl as defined herein linked through amino having a free valence bond from the nitrogen atom e.g. benzyloxycarbonylamino, phenethoxycarbonylamino, 3-phenylpropoxycarbonylamino, 1-naphthylmethoxycarbonylamino, 2-(1-naphtyl)ethoxycarbonylamino and the like.

The term "aryl" is intended to include aromatic rings, such as carboxylic aromatic rings selected from the group consisting of phenyl, naphthyl, (1-naphtyl or 2-naphtyl) and the like optionally substituted with halogen, amino, hydroxy, $C_{1-6}$-alkyl or $C_{1-6}$-alkoxy and the like.

The term "arylene" is intended to include divalent aromatic rings, such as carboxylic aromatic rings selected from the group consisting of phenylene, naphthylene and the like optionally substituted with halogen, amino, hydroxy, $C_{1-6}$-alkyl or $C_{1-6}$-alkoxy and the like.

The term "halogen" means fluorine, chlorine, bromine or iodine.

The term "perhalomethyl" means trifluoromethyl, trichloromethyl, tribromomethyl or triiodomethyl.

The term "$C_{1-6}$-dialkylamino" as used herein refers to an amino group wherein the two hydrogen atoms independently are substituted with a straight or branched, saturated hydrocarbon chain having the indicated number of carbon atoms; such as dimethylamino, N-ethyl-N-methylamino, diethylamino, dipropylamino, N-(n-butyl)-N-methylamino, di(n-pentyl)amino and the like.

The term "acyl" as used herein refers to a monovalent substituent comprising a $C_{1-6}$-alkyl group linked through a carbonyl group; such as e.g. acetyl, propionyl, butyryl, isobutyryl, pivaloyl, valeryl and the like.

The term "acyloxy" as used herein refers to acyl as defined herein linked to an oxygen atom having its free valence bond from the oxygen atom e.g. acetyloxy, propionyloxy, butyryloxy, isobutyryloxy, pivaloyloxy, valeryloxy and the like.

The term "$C_{1-12}$-alkoxycarbonyl" as used herein refers to a monovalent substituent comprising a $C_{1-12}$-alkoxy group linked through a carbonyl group; such as e.g. methoxycarbonyl, carbethoxy, propoxycarbonyl, isopropoxycarbonyl, n-butoxycarbonyl, sec-butoxycarbonyl, tert-butoxycarbonyl, 3-methylbutoxycarbonyl, n-hexoxycarbonyl and the like.

The term "bicycloalkyl" as used herein refers to a monovalent substituent comprising a bicyclic structure made of 6–12 carbon atoms such as e.g. 2-norbornyl, 7-norbornyl, 2-bicyclo[2.2.2]octyl and 9-bicyclo[3.3.1]nonanyl and the like.

The term "heteroaryl" as used herein, alone or in combination, refers to a monovalent substituent comprising a 5–6 membered monocyclic aromatic system or a 9–10 membered bicyclic aromatic system containing one or more heteroatoms selected from nitrogen, oxygen and sulfur, e.g. furan, thiophene, pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine and the like.

The term "heteroarylene" as used herein, alone or in combination, refers to a divalent group comprising a 5–6 membered monocyclic aromatic system or a 9–10 membered bicyclic aromatic system containing one or more heteroatoms selected from nitrogen, oxygen and sulfur, e.g. furan, thiophene, pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine and the like.

The term "heteroaryloxy" as used herein, alone or in combination, refers to a heteroaryl as defined herein linked to an oxygen atom having its free valence bond from the oxygen atom e.g. pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine linked to oxygen, and the like.

The term "arylalkyl" as used herein refers to a straight or branched saturated carbon chain containing from 1 to 6 carbons substituted with an aromatic carbohydride; such as benzyl, phenethyl, 3-phenylpropyl, 1-naphthylmethyl, 2-(1-naphtyl)ethyl and the like.

The term "aryloxy" as used herein refers to phenoxy, 1-naphthyloxy, 2-naphthyloxy and the like.

The term "arylalkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like.

The term "heteroarylalkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrimidyl)ethyl and the like.

The term "heteroarylalkoxy" as used herein refers to a heteroarylalkyl as defined herein linked to an oxygen atom having its free valence bond from the oxygen atom, e.g. (2-furyl)methyl, (3-furyl)methyl, (2-thienyl)methyl, (3-thienyl)methyl, (2-pyridyl)methyl, 1-methyl-1-(2-pyrimidyl)ethyl linked to oxygen, and the like.

The term "$C_{1-6}$-alkylsulfonyl" as used herein refers to a monovalent substituent comprising a $C_{1-6}$-alkyl group linked through a sulfonyl group such as e.g. methylsulfonyl, ethylsulfonyl, n-propylsulfonyl, isopropylsulfonyl, n-butylsulfonyl, sec-butylsulfonyl, isobutylsulfonyl, tert-butylsulfonyl, n-pentylsulfonyl, 2-methylbutylsulfonyl, 3-methylbutylsulfonyl, n-hexylsulfonyl, 4-methylpentylsulfonyl, neopentylsulfonyl n-hexylsulfonyl, 2,2-dimethylpropylsulfonyl and the like.

The term "$C_{1-6}$-monoalkylaminosulfonyl" as used herein refers to a monovalent substituent comprising a $C_{1-6}$- monoalkylamino group linked through a sulfonyl group such as e.g. methylaminosulfonyl, ethylaminosulfonyl, n-propylaminosulfonyl, isopropylaminosulfonyl, n-obutylamino sulfonyl, sec-butylaminosulfonyl, isobutylaminosulfonyl, tert-butylaminosulfonyl, n-pentylaminosulfonyl, 2-methylbutylaminosulfonyl, 3-methylbutylaminosulfonyl, n-hexylaminosulfonyl, 4-methylpentylaminosulfonyl, neopentylaminosulfonyl, n-hexylaminosulfonyl, 2,2-dimethylpropylaminosulfonyl and the like.

The term "$C_{1-6}$-dialkylaminosulfonyl" as used herein refers to a monovalent substituent comprising a $C_{1-6}$-dialkylamino group linked through a sulfonyl group such as dimethylaminosulfonyl, N-ethyl-N-methylaminosulfonyl, diethylaminosulfonyl, dipropylaminosulfonyl, N-(n-butyl)-N-methylaminosulfonyl, di(n-pentyl) aminosulfonyl and the like.

The term "acylamino" as used herein refers to an amino group wherein one of the hydrogen atoms is substituted with an acyl group, such as e.g. acetamido, propionamido, isopropylcarbonylamino and the like.

The term "$(C_{3-6}$-cycloalkyl$)C_{1-6}$-alkyl" as used herein, alone or in combination, refers to a straight or branched, saturated hydrocarbon chain having 1 to 6 carbon atoms and being monosubstituted with a $C_{3-6}$-cycloalkyl group, the cycloalkyl group optionally being mono- or polysubstituted with $C_{1-6}$-akyl, halogen, hydroxy or $C_{1-6}$-alkoxy ; such as e.g. cyclopropylmethyl, (1-methylcyclopropyl)methyl, 1-(cyclopropyl)-ethyl, cyclopentylmethyl, cyclohexylmethyl and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy; e.g. phenylthio, (4-methylphenyl)-thio, (2-chlorophenyl)thio and the like.

The term "arylsulfonyl" as used herein refers to an aryl group linked through a sulfonyl group, the aryl group optionally being mono- or polysubstituted with $C_{1-6}$-alkyl, halogen, hydroxy or $C_{1-6}$-alkoxy; such as e.g. phenylsulfonyl, tosyl and the like.

The term "$C_{1-6}$-monoalkylaminocarbonyl" as used herein refers to a monovalent substituent comprising a $C_{1-6}$-monoalkylamino group linked through a carbonyl group such as e.g. methylaminocarbonyl, ethylaminocarbonyl, n-propylaminocarbonyl, isopropylaminocarbonyl, n-butylaminocarbonyl, sec-butylaminocarbonyl, isobutylaminocarbonyl, tert-butylaminocarbonyl, n-pentylaminocarbonyl, 2-methylbutylaminocarbonyl, 3-methylbutylaminocarbonyl, n-hexylaminocarbonyl, 4-methylpentylaminocarbonyl, neopentylaminocarbonyl, n-hexylaminocarbonyl, 2-2-dimethylpropylaminocarbonyl and the like.

The term "$C_{1-6}$-dialkylaminocarbonyl" as used herein refers to a monovalent substituent comprising a $C_{1-6}$-dialkylamino group linked through a carbonyl group such as dimethylaminocarbonyl, N-ethyl-N-methylaminocarbonyl, diethylaminocarbonyl, dipropylaminocarbonyl, N-(n-butyl)-N-methylaminocarbonyl, di(n-pentyl)aminocarbonyl and the like.

As used herein, the phrase "heterocyclyl" means a monovalent saturated or unsaturated non aromatic group being monocyclic and containing one or more, such as from one to four carbon atom(s), and from one to four N, O or S atom(s) or a combination thereof. The phrase "heterocyclyl" includes, but is not limited to, 5-membered heterocycles having one hetero atom (e.g. pyrrolidine, pyrroline and the like); 5-membered heterocycles having two heteroatoms in 1,2 or 1,3 positions (e.g. pyrazoline, pyrazolidine, 1,2-oxathiolane, imidazolidine, imidazoline, 4-oxazolone and the like); 5-membered heterocycles having three heteroatoms (e.g. tetrahydrofurazan and the like); 5-membered heterocycles having four heteroatoms; 6-membered heterocycles with one heteroatom (e.g. piperidine and the like); 6-membered heterocycles with two heteroatoms (e.g. piperazine, morpholine and the like); 6-membered heterocycles with three heteroatoms; and 6-membered heterocycles with four heteroatoms, and the like.

As used herein, the phrase "a divalent heterocyclic group" means a divalent saturated or unsaturated system being monocyclic and containing one or more, such as from one to four carbon atom(s), and one to four N, O or S atom(s) or a combination thereof. The phrase a divalent heterocyclic group includes, but is not limited to, 5-membered heterocycles having one hetero atom (e.g. pyrrolidine, pyrroline and the like); 5-membered heterocycles having two heteroatoms in 1,2 or 1,3 positions (e.g. pyrazoline, pyrazolidine, 1,2-oxathiolane, imidazolidine, imidazoline, 4-oxazolone and the like); 5-membered heterocycles having three heteroatoms (e.g. tetrahydrofurazan and the like); 5-membered heterocycles having four heteroatoms; 6-membered heterocycles with one heteroatom (e.g. piperidine and the like); 6-membered heterocycles with two heteroatoms (e.g. piperazine, morpholine and the like); 6-membered heterocycles with three heteroatoms; and 6-membered heterocycles with four heteroatoms, and the like.

As used herein, the phrase "a 5–6 membered cyclic ring" means an unsaturated or saturated or aromatic system containing one or more carbon atoms and optionally from one to four N, O or S atom(s) or a combination thereof. The phrase "a 5–6 membered cyclic ring" includes, but is not limited to, e.g. cyclopentyl, cyclohexyl, phenyl, cyclohexenyl, pyrrolidinyl, pyrrolinyl, imidazolidinyl, pyrazolidinyl, pyrazolinyl, piperidyl, piperazinyl, pyrrolyl, 2H-pyrrolyl, imidazolyl, pyrazolyl, triazolyl, pyridyl, pyrazinyl, pyrimidinyl, pyridazinyl, morpholinyl, thiomorpholinyl, isothiazolyl, isoxazolyl, oxazolyl, oxadiazolyl, thiadiazolyl, 1,3-dioxolanyl, 1,4-dioxolanyl and the like, 5-membered heterocycles having one hetero atom (e.g. thiophenes, pyrroles, furans and the like); 5-membered heterocycles having two heteroatoms in 1,2 or 1,3 positions (e.g. oxazoles, pyrazoles, imidazoles, thiazoles, purines and the like); 5-membered heterocycles having three heteroatoms (e.g. triazoles, thiadiazoles and the like); 5-membered heterocycles having four heteroatoms; 6-membered heterocycles with one heteroatom (e.g. pyridine, quinoline, isoquinoline, phenanthridine, cyclohepta[b]pyridine and the like); 6-membered heterocycles with two heteroatoms (e.g. pyridazines, cinnolines, phthalazines, pyrazines, pyrimidines, quinazolines, morpholines and the like); 6-membered heterocycles with three heteroatoms (e.g. 1,3,5-triazine and the like); and 6-membered heterocycles with four heteroatoms and the like.

Certain of the above defined terms may occur more than once in the above formula (I), and upon such occurence each term shall be defined independently of the other.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts whereever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). More specifically the compound of formula I may be converted to a 1:1 mixture of diastereomeric amides by treating with chiral amines, amino acids, amino alcohols derived from amino acids; conventional reaction conditions may be employed to convert acid into an amide; the dia-streomers may be separated either by fractional crystallization or chromatography and the stereoisomers of compound of formula I may be prepared by hydrolysing the pure diastereomeric amide.

Various polymorphs of compound of general formula I forming part of this invention may be prepared by crystallization of compound of formula I under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

Furthermore, the present compounds of formula I can be utilised in the treatment and/or prevention of conditions mediated by nuclear receptors, in particular the Peroxisome Proliferator-Activated Receptors (PPAR).

In a further aspect, the present invention relates to a method of treating and/or preventing Type I or Type II diabetes.

In a still further aspect, the present invention relates to the use of one or more compounds of the general formula I or pharmaceutically acceptable salts thereof for the preparation of a medicament for the treatment and/or prevention of Type I or Type II diabetes.

In a still further aspect, the present compounds are useful for the treatment and/or prevention of IGT.

In a still further aspect, the present compounds are useful for the treatment and/or prevention of Type 2 diabetes.

In a still further aspect, the present compounds are useful for the delaying or prevention of the progression from IGT to Type 2 diabetes.

In a still further aspect, the present compounds are useful for the delaying or prevention of the progression from non-insulin requiring Type 2 diabetes to insulin requiring Type 2 diabetes.

In another aspect, the present compounds reduce blood glucose and triglyceride levels and are accordingly useful for the treatment and/or prevention of ailments and disorders such as diabetes and/or obesity.

In still another aspect, the present compounds are useful for the treatment and/or prophylaxis of insulin resistance (Type 2 diabetes), impaired glucose tolerance, dyslipidemia, disorders related to Syndrome X such as hypertension, obesity, insulin resistance, hyperglycaemia, atherosclerosis, hyperlipidemia, coronary artery disease, myocardial ischemia and other cardiovascular disorders.

In still another aspect, the present compounds are effective in decreasing apoptosis in mammalian cells such as beta cells of Islets of Langerhans.

In still another aspect, the present compounds are useful for the treatment of certain renal diseases including glomerulonephritis, glomerulosclerosis, nephrotic syndrome, hypertensive nephrosclerosis.

In still another aspect, the present compounds may also be useful for improving cognitive functions in dementia, treating diabetic complications, psoriasis, polycystic ovarian syndrome (PCOS) and prevention and treatment of bone loss, e.g. osteoporosis.

The invention also relates to pharmaceutical compositions comprising, as an active ingredient, at least one compound of the formula I or any optical or geometric isomer or tautomeric form thereof including mixtures of these or a pharmaceutically acceptable salt thereof together with one or more pharmaceutically acceptable carriers or diluents.

Furthermore, the invention relates to the use of compounds of the general formula I or their tautomeric forms, their stereoisomers, their polymorphs, their pharmaceutically acceptable salts or pharmaceutically acceptable solvates thereof for the preparation of a pharmaceutical composition for the treatment and/or prevention of conditions mediated by nuclear receptors, in particular the Peroxisome Proliferator-Activated Receptors (PPAR) such as the conditions mentioned above.

The present invention also relates to a process for the preparation of the above said novel compounds, their derivatives, their analogs, their tautomeric forms, their stereoisomers, their polymorphs, their pharmaceutically acceptable salts or pharmaceutically acceptable solvates.

A compound of formula I can be prepared as described below:

a) Reacting a compound of formula II wherein A, B, T, X, Y, and p are as defined previously, except that T is not N,

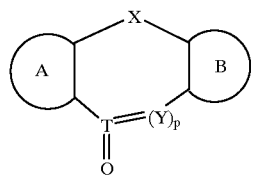

(II)

through a Wittig process with $(PH_3P)_3P(CH_2)_{n+1}OH.Br$ in the presence of a suitable base as butyllithium, to give compounds of formula III.

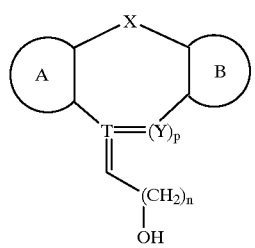

(III)

wherein A, B, X, Y, T, p and n are defined as previously, except that T is not N. Compounds of formula III may then be reacted under Mitsunobu conditions with compounds of formula IV

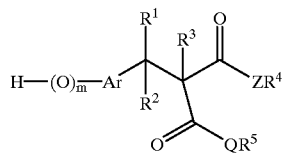

(IV)

wherein m, $R^1$, $R^2$, $R^3$ are defined as previously and wherein $R^4$ and $R^5$ are defined as previously except H, to give compounds of formula wherein A, B, X, Y, T, Ar, Z, Q, p, n, $R^1$, $R^2$, $R^3$ are defined as previously, except that T is not N, and wherein $R^4$ and $R^5$ are defined as previously except H, and wherein m and k is 1 and within the term T===$(Y)_p$, === is defined as a single bond and within the term T===$(CH_k)$, === is defined as a double bond.

b) Alternatively a compound of formula V

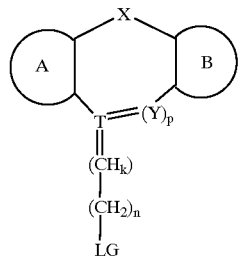

(V)

wherein A, B, X, Y, T, p, n, k and the terms T===$(Y)_p$ and T===$(CH_k)$ are defined as previously and wherein LG is a suitable leaving group, may be reacted, possible under transition metal catalysis, with a nucleophilic compound of formula VI

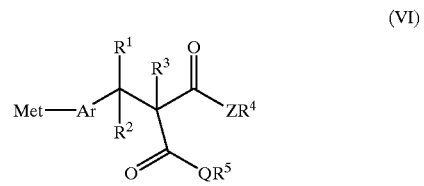

(VI)

wherein Ar, $R^1$, $R^2$, $R^3$ are defined as previously and wherein $R^4$ and $R^5$ are defined as previously except H and wherein "Met" is a metal such as zinc or copper, carrying suitable ligands preferentially from trifluoro-methanesulfonate or halide to give compounds of formula I, wherein A, B, X, Y, T, Ar, Z, Q, p, n, $R^1$, $R^2$, $R^3$, and the terms T===$(Y)_p$ and T===$(CH_k)$ are defined as previously and wherein $R^4$ and $R^5$ are defined as previously except H, and wherein m is 0.

c) Alternatively compounds of formula V wherein A, B, X, Y, T, p, n, and the terms T===$(Y)_p$ and T===$(CH_k)$ are defined as previously and wherein LG is a suitable leaving group (for example halogen, sulfonates, phosphor, hydroxy under Mitsunobu conditions) are reacted with a compound of VII (VII)

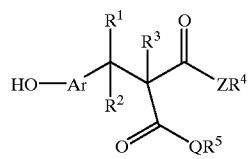

wherein Ar, Z, Q, $R^1$, $R^2$, $R^3$ are defined as previously and wherein $R^4$ and $R^5$ are defined as previously except H, to give compounds of formula I wherein A, B, X, Y, T, Ar, Z, Q, p, n, $R^1$, $R^2$, $R^3$, and the terms T===$(Y)_p$ and T===$(CH_k)$ are defined as previously and wherein $R^4$ and $R^5$ are defined as previously except H, and wherein m is 1.

d) Alternatively a compound of formula VIII (VIII)

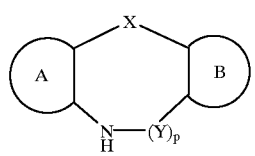

wherein A, B, X, Y and p are defined as previously, may be alkylated with a suitable electrophilic reagent such as ethylene oxide, ethyl bromoacetate followed by reduction of the ester to an alcohol, 2-bromoethanol or 2-bromoethanol to give a compound of formula X (X)

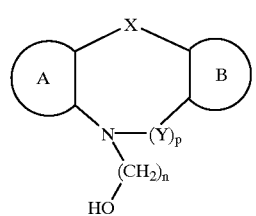

wherein A, B, X, Y, p and n are defined as previously. The hydroxy group can if needed be converted to a suitable leaving group and reacted with a compound of formula VII, wherein Ar, Z, Q, $R^1$, $R^2$, $R^3$ are defined as previously and wherein $R^4$ and $R^5$ are defined as previously except H, to give compounds of formula I, wherein A, B, X, Y, Ar, Z, Q, p, n, $R^1$, $R^2$ and $R^3$ are defined as previously and within the terms T===$(Y)_p$ and T===$(CH_k)$, === is defined as a singlebond and wherein $R^4$ and $R^5$ are defined as previously except H, and wherein m is 1 and k is 0 and wherein T is N.

e) Alternatively reacting compounds of formula X wherein A, B, X, Y, p and n are defined as previously, with a compound of formula XI (XI)

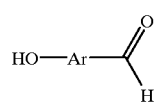

wherein Ar is defined as previously followed by reaction with a suitable Wittig reagent to give a compound of formula XII (XII)

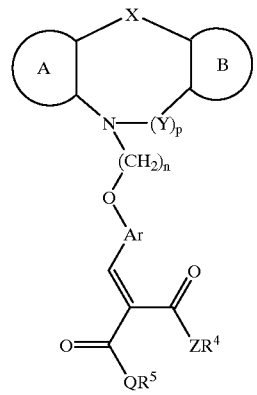

wherein A, B, X, Y, Ar, Z, Q, p, n, $R^1$, $R^2$, $R^3$, and the terms T===$(Y)_p$ and T===$(CH_k)$ are defined as previously and wherein $R^4$ and $R^5$ are defined as previously except H. Addition to the double bond of suitable reagents give compounds of formula III wherein A, B, X, Y, Ar, Z, Q, p, n, $R^1$, $R^2$ and $R^3$ are defined as previously and within the terms T===$(Y)_p$ and T===$(CH_k)$, is defined as a single bond and wherein $R^4$ and $R^5$ are defined as previously except H, and wherein m is 1 and k is 0 and wherein T is N.

f) Alternatively compounds of formula I wherein A, B, X, Y, T, Ar, p, n, k, $R^1$, $R^2$, $R^3$, and the terms T===$(Y)_p$ and T===$(CH_k)$ are defined as previously and wherein Z and Q is O and wherein $R^4$ and $R^5$ are defined as previously except H can either be hydrolysed to the corresponding acid or be reacted further to give a compound of formula I wherein A, B, X, Y, T, Ar, Z, Q, p, n, $R^1$, $R^2$, $R^3$, $R^4$, $R^5$ and the terms T===$(Y)_p$ and T===$(CH_k)$, are defined as previously.

Pharmacological Methods

In vitro PPAR alpha and PPAR gamma activation activity.

Principle

The PPAR gene transcription activation assays were based on transient transfection into human HEK293 cells of two plasmids encoding a chimeric test protein and a reporter protein respectively. The chimeric test protein was a fusion of the DNA binding domain (DBD) from the yeast GAL4 transcription factor to the ligand binding domain (LBD) of the human PPAR proteins. The PPAR LBD harbored in addition to the ligand binding pocket also the native activation domain (activating function 2=AF2) allowing the fusion protein to function as a PPAR ligand dependent transcription factor. The GAL4 DBD will force the fusion protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand, luciferase protein will be produced in amounts corresponding to the activation of the PPAR protein. The amount of luciferase protein is measured by light emission after addition of the appropriate substrate.

Methods

Cell culture and transfection: HEK293 cells were grown in DMEM+10% FCS, 1% PS. Cells were seeded in 96-well plates the day before transfection to give a confluency of 80% at transfection. 0.8 µg DNA per well was transfected using FuGene transfection reagent according to the manufacturers instructions (Boehringer-Mannheim). Cells were allowed to express protein for 48 h followed by addition of compound.

Plasmids: Human PPAR α and γ was obtained by PCR amplification using cDNA templates from liver, intestine and adipose tissue respectively. Amplified cDNAs were cloned into pCR2.1 and sequenced. The LBD from each isoform PPAR was generated by PCR (PPARα: aa 167—C-term; PPARγ: aa 165—C-term) and fused to GAL4-DBD by subcloning fragments in frame into the vector pM1 generating the plasmids pM1αLBD and pM1γLBD. Ensuing fusions were verified by sequencing. The reporter was constructed by inserting an oligonucleotide encoding five repeats of the Gal4 recognition sequence into the pGL2 vector (Promega).

Compounds: All compounds were dissolved in DMSO and diluted 1:1000 upon addition to the cells. Cells were treated with compound (1:1000 in 200 μgrowth medium including delipidated serum) for 24 h followed by luciferase assay.

Luciferase assay: Medium including test compound was aspirated and 100 μl PBS incl. 1 mM Mg++ and Ca++ was added to each well. The luciferase assay was performed using the LucLite kit according to the manufacturers instructions (Packard Instruments). Light emission was quantified by counting SPC mode on a Packard Instruments topcounter.

Pharmaceutical Compositions

In another aspect, the present invention includes within its scope pharmaceutical compositions comprising, as an active ingredient, at least one of the compounds of the general formula I or a pharmaceutically acceptable salt thereof together with a pharmaceutically acceptable carrier or diluent.

The present compounds may also be administered in combination with one or more further pharmacologically active substances eg. selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, RXR agonists and agents acting on the ATP-dependent potassium channel of the β-cells.

In one embodiment of the invention the present compounds are administered in combination with insulin.

In a further embodiment the present compounds are administered in combination with a sulphonylurea eg. tolbutamide, glibenclamide, glipizide or glicazide.

In another embodiment the present compounds are administered in combination with a biguanide eg. metformin.

In yet another embodiment the present compounds are administered in combination with a meglitinide eg. repaglinide.

In a further embodiment the present compounds are administered in combination with an α-glucosidase inhibitor eg. miglitol or acarbose.

In another embodiment the present compounds are administered in combination with an agent acting on the ATP-dependent potassium channel of the β-cells eg. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent eg. cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds eg. in combination with a sulphonylurea and metformin, a sulphonylurea and acarbose, repaglinide and metformin, insulin and a sulphonylurea, insulin and metformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

Pharmaceutical compositions containing a compound of the present invention may be prepared by conventional techniques, e.g. as described in Remington: The Science and Practise of Pharmacy, 19$^{th}$ Ed., 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of diseases related to the regulation of blood sugar.

Such mammals include also animals, both domestic animals, e.g. household pets, and non-domestic animals such as wildlife.

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients it may frequently be necessary to begin with a dosage of from about 2 to about 70 mg per day and when the condition is under control to reduce the dosage as low as from about 0.1 to about 10 mg per day. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 0.1 to about 100 mg of active ingredient togetherwith a pharmaceutically acceptable carrier per unit dosage.

Usually, dosage forms suitable for oral, nasal, pulmonary or transdermal administration comprise from about 0.001 mg to about 100 mg, preferably from about 0.01 mg to about 50 mg of the compounds of formula I admixed with a pharmaceutically acceptable carrier or diluent.

Any novel feature or combination of features described herein is considered essential to this invention.

EXAMPLES

The process for preparing compounds of formula I and preparations containing them is further illustrated in the following examples, which however, are not to be construed as limiting.

The structures of the compounds are confirmed by either elemental analysis (MA) nuclear magnetic resonance (NMR) or mass spectrometry (MS). NMR shifts (d) are given in parts per million (ppm) and only selected peaks are given. mp is melting point and is given in ° C. Column chromatography was carried out using the technique described by W. C. Still et al, J. Org. Chem. 1978, 43, 2923–2925 on Merck silica gel 60 (Art 9385). Compounds used as starting materials are either known compounds or compounds which can readily be prepared by methods known per se.

| Abbrevations: | |
|---|---|
| TLC: | thin layer chromatography |
| DMSO: | dimethylsulfoxide |
| CDCl$_3$: | deutorated chloroform |
| DMF: | N,N-dimethylformamide |
| min: | minutes |
| h: | hours |

Example 1

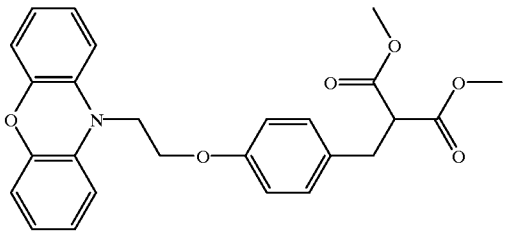

2-[2-Phenoxazine-10-yl-ethoxy)-benzyl]-malonic acid dimethyl ester a)

A solution of benzyloxybenzaldehyde (10.6 g, 50.0 mmol) and dimethyl malonate (6.6 g, 50.0 mmol) in benzene (100 mL) containing a catalytic quantity of pipiridinium acetate was refluxed in a Dean-Stark trap for 16 h. After cooling to room temperature, the solution was concentrated. The residue was crystallised from ethyl acetate/heptane to give 14.5 g (90%) of 2-(4-benzyloxy-benzylidene)-malonic acid dimethyl ester: mp 134–135° C. $^1$H NMR (300 MHz, CDCl$_3$): δ3.82 (s, 3H), 3.86 (s, 3H), 5.08 (s, 2H), 6.95 (d, 2H), 7.30–7.45 (m, 7H), 7.70 (s, 1H)

b)

A solution of 2-(4-benzyloxy-benzylidene)-malonic acid dimethyl ester (14.5 g, 44.5 mmol) in methanol (300 mL) was hydrogenated at 3 atm. in the presence of 5% palladium on charcoal (1.1 g). The solution was filtered, and the filtrate evaporated under a vacuum to give 9.2 g (77%) of 2-(4-hydroxy-benzyl)-malonic acid dimethyl ester: $^1$H NMR (300 MHz, CDCl$_3$): δ3.15 (d, 2H), 3.65 (t, 1H), 3.70 (s, 6H), 6.70 (d, 2H), 7.05 (d, 2H).

c)

Under a nitrogen atmosphere, 2-phenoxazin-10-yl-ethanol (340 mg, 1.5 mmol), tributylphosphine (455 mg, 2.25 mmol) and 2-(4-hydroxy-benzyl)-malonic acid dimethyl ester (357 mg, 1.5 mmol) were successively dissolved in dry benzene (20 mL). Solid azodicarboxylic dipiperidide (ADDP) (567 mg, 2.25 mmol) was added under stirring at 0° C. to the solution. After 10 min, the reaction mixture was brought to room temperature and the stirring was continued for 2 h. Heptane (10 mL) was added to the reaction mixture and dihydro-ADDP separated out was filtered off. After evaporation of the solvent the product was purified by flash chromatography gradiating from toluen to toluen/ethyl acetate (19:1). The title compound was isolated as a crystalline product (325 mg, 48%): mp 100–101° C.; $^1$H NMR (300 MHz, CDCl$_3$): δ3.15 (d, 2H), 3.62 (t, 1H), 3.68 (s, 6H), 3.95 (t, 2H), 4.15 (t, 2H) 6.58–6.70 (m, 6H), 6.75–6.84 (m, 4H), 7.10 (d, 2H)

Example 2

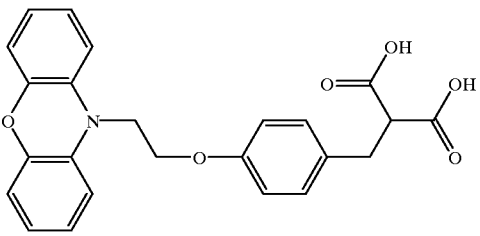

2-[4-(2-Phenoxazine-10-yl-ethoxy)-benzyl]-malonic acid, disodiumsalt

A 1 N aqueous solution of sodium hydroxide (3 mL) was added to a solution of 2-{4-(2-phenoxazine-10-yl-ethoxy)-benzyl]-malonic acid dimethyl ester (150 mg, 0.3 mmol) in a mixture of methanol (3 mL) and tetrahydrofuran (3 mL). The mixture was stirred for 64 h at room temperature. The title compound (95 mg, 72%) was isolated by filtration and washed with a mixture of MeOH/THF: mp 303–307° C.; $^1$H NMR (300 MHz, D$_2$O): δ2.96 (d, 2H), 3.35 (t, 1H), 3.75–3.95 (bs, 2H), 4.18 (m, 2H), 6.55–6.90 (m, 10H), 7.15 (d, 2H).

What is claimed is:

1. A compound of formula (I)

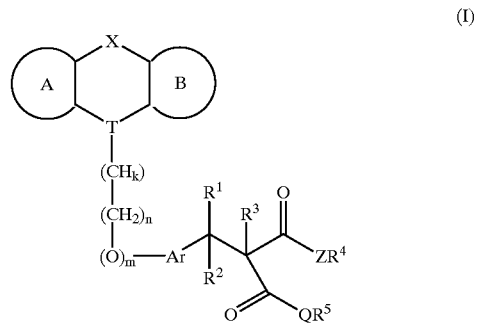

wherein ring A and ring B, fused to the ring containing X and T, independently of each other represents a phenyl ring, optionally substituted with one or more halogen, perhalomethyl, hydroxy, nitro, cyano, formyl, or $C_{1-12}$-alkyl, $C_{4-12}$-alkenynyl, $C_{2-12}$-alkenyl, $C_{2-12}$-alkynyl, $C_{1-12}$-alkoxy, aryloxy, arylalkyl, arylalkoxy, heteroarylalkyl, heteroaryloxy, heteroarylalkoxy, acyl, acyloxy, hydroxy$C_{1-12}$-alkyl, amino, acylamino, $C_{1-12}$-alkyl-amino, arylamino, arylalkylamino, amino-$C_{1-12}$-alkyl, $C_{1-12}$-alkoxycarbonyl, aryloxycarbonyl, arylalkoxycarbonyl, $C_{1-12}$-alkoxyC$_{1-12}$-alkyl, aryloxy$C_{1-12}$-alkyl, arylalkoxy$C_{1-12}$-alkyl, $C_{1-12}$- alkylthio, thioC$_{1-12}$-alkyl, C$_{1-12}$-alkoxycarbonylamino, aryloxycarbonylamino, arylalkoxycarbonylamino, bicycloalkyl, (C$_{3-6}$-cycloalkyl)C$_{1-6}$-alkyl, C$_{1-6}$-dialkylamino, C$_{1-6}$-alkylsulfonyl, C$_{1-6}$-monoalkylaminosulfonyl, C$_{1-6}$-dialkylaminosulfonyl, arylthio, arylsulfonyl, C$_{1-6}$-monoalkylaminocarbonyl, C$_{1-6}$-dialkylaminocarbonyl, —COR$^6$ or —SO$_2$R$^7$, wherein R$^6$ and R$^7$ independently of each other are selected from hydroxy, halogen, perhalomethyl, C$_{1-6}$-alkoxy or amino optionally substituted with one or more C$_{1-6}$-alkyl or perhalomethyl;

X is —O—;

T is N;

k is 2;

Ar represents arylene, heteroarylene, or a divalent heterocyclic group each of which can optionally be substituted with one or more halogen, C$_{1-6}$-alkyl, amino, hydroxy, C$_{1-6}$-alkoxy or aryl;

R$^1$ represents hydrogen, hydroxy, halogen, C$_{1-12}$-alkoxy, C$_{1-12}$-alkyl, C$_{4-12}$-alkenynyl, C$_{2-12}$-alkenyl, C$_{2-12}$-alkynyl or arylalkyl; optionally substituted with one or more halogen, perhalomethyl, hydroxy, nitro or cyano;

R$^2$ represents hydrogen, hydroxy, halogen, C$_{1-12}$-alkoxy, C$_{1-2}$-alkyl, C$_{4-12}$-alkenynyl, C$_{1-2}$-alkenyl, C$_{2-12}$-alkynyl or arylalkyl; optionally substituted with one or more halogen, perhalomethyl, hydroxy, nitro or cyano; or R$^2$ forms a bond together with R$^3$;

R$^3$ represents hydrogen, hydroxy, halogen, C$_{1-12}$-alkoxy, C$_{1-12}$-alkyl, C$_{4-12}$-alkenynyl, C$_{2-12}$-alkenyl, C$_{2-12}$-alkynyl, acyl or arylalkyl; optionally substituted with one or more halogen, perhalomethyl, hydroxy, nitro or cyano; or R$^3$ forms a bond together with R$^2$;

R$^4$ represents hydrogen, C$_{1-12}$-alkyl, C$_{4-12}$-alkenynyl, C$_{2-12}$-alkenyl, C$_{2-12}$-alkynyl, aryl, arylalkyl heterocyclyl, heteroaryl or heteroarylalkyl groups; optionally substituted with one or more halogen, perhalomethyl, hydroxy, nitro or cyano;

R$^5$ represents hydrogen, C$_{1-12}$-alkyl, C$_{4-12}$-alkenynyl, C$_{2-12}$-alkenyl, C$_{2-12}$-alkynyl, aryl, arylakyl, heterocyclyl, heteroaryl or heteroarylalkyl groups; optionally substituted with one or more halogen, perhalomethyl, hydroxy, nitro or cyano;

Z represents oxygen or NR$^{12}$, wherein R$^{12}$ represents hydrogen C$_{1-12}$-alkyl, aryl, hydroxyC$_{1-12}$-alkyl or arylalkyl groups or when Z is NR$^{12}$, R$^4$ and R$^{12}$ may form a 5 or 6 membered nitrogen containing ring, optionally substituted with one or more C$_{1-6}$-alkyl;

Q represents oxygen or NR$^{13}$, wherein R$^{13}$ represents hydrogen C$_{1-12}$-alkyl, aryl, hydroxyC$_{1-12}$-alkyl or arylalkyl groups or when Q is NR$^3$, R$^5$ and R$^{13}$ may form a 5 or 6 membered nitrogen containing ring, optionally substituted with one or more C$_{1-6}$-alkyl;

n is an integer ranging from 0 to 3;

m is an integer ranging from 0 to 1;

or a salt thereof with a pharmaceutically acceptable acid or base, or any optical isomer or mixture of optical isomers, or any tautomeric forms.

2. The compound of claim 1 wherein ring A and ring B, fused to the ring containing X and T independently of each other represents a phenyl ring, optionally substituted with halogen, C$_{1-6}$-alkyl or aryl, wherein the aryl can be substituted with one or more halogen or C$_{1-6}$-alkyl.

3. The compound of claim 1 wherein ring A and ring B, fused to the ring containing X and T independently of each other represents a phenyl ring.

4. The compound of claim 1 wherein Ar represents arylene.

5. The compound of claim 1 wherein R$^1$, R$^2$ and R$^3$ represents hydrogen.

6. The compound of claim 1 wherein R$^4$ and R$^5$ represents hydrogen or methyl.

7. The compound of claim 1 wherein Z and Q represents O.

8. The compound of claim 1 wherein n is 1.

9. The compound of claim 1 wherein m is 1.

10. The compound of claim 1 comprising

2-{4-(2-Phenoxazine-10-yl-ethoxy)-benzyl]-malonic acid dimethyl ester,

2-{4-(2-Phenoxazine-10-yl-ethoxy)-benzyl]-malonic acid;

or a salt thereof with a pharmaceutically acceptable acid or base, or any optical isomer or mixture of optical isomers, or any tautomeric forms.

11. A pharmaceutical composition comprising, as an active ingredient, the compound of claim 1, or a pharmaceutically acceptable salt thereof, together with a pharmaceutically acceptable carrier or diluent.

12. The composition of claim 11 in unit dosage form, comprising from 0.05 to 100 mg of the compound or a pharmaceutically acceptable salt thereof.

13. A method for the treatment of diabetes and/or obesity, the method comprising administering to a subject in need thereof an effective amount of the compound of claim 1.

14. The compound of claim 1, wherein the mixture of optical isomers is a racemic mixture.

15. The compound of claim 10, wherein the mixture of optical isomers is a racemic mixture.

16. The composition of claim 12, comprising from 0.1 to 50 mg of the compound or a pharmaceutically acceptable salt thereof.

* * * * *